United States Patent [19]

Harrison

[11] Patent Number: 5,558,374
[45] Date of Patent: Sep. 24, 1996

[54] CONTACT LENS APPLICATOR

[76] Inventor: Kenneth Harrison, 813 Sussex Rd., Franklin Lakes, N.J. 07417

[21] Appl. No.: 388,554

[22] Filed: Feb. 13, 1995

Related U.S. Application Data

[63] Continuation-in-part of Ser. No. 279,253, Jul. 21, 1994, Pat. No. 5,407,241.

[51] Int. Cl.⁶ .................................................. A61F 9/00
[52] U.S. Cl. ............................................................. 294/1.2
[58] Field of Search .............................. 294/1.2; 15/214; 134/901; 206/5.1; 606/107

[56] References Cited

U.S. PATENT DOCUMENTS

| | | | |
|---|---|---|---|
| 2,919,696 | 1/1960 | Rinaldy | 294/1.2 |
| 3,054,412 | 9/1962 | Nickell | 206/5.1 X |
| 3,091,328 | 5/1963 | Leonardos | 294/1.2 X |
| 3,177,874 | 4/1965 | Spriggs | 294/1.2 |
| 3,343,657 | 9/1967 | Speshyock | 206/5.1 X |
| 3,344,461 | 10/1967 | Floor | 294/1.2 X |
| 3,645,284 | 2/1972 | Krezanoski et al. | 134/901 X |
| 3,990,579 | 11/1976 | Manning | 134/901 X |
| 4,026,591 | 5/1977 | Cleaveland | 294/1.2 |
| 4,113,297 | 9/1978 | Quinn | 294/1.2 |
| 4,308,947 | 1/1982 | Arnhem | 294/1.2 X |
| 4,392,569 | 7/1983 | Shoup | 206/5.1 |
| 4,565,396 | 1/1986 | Larimer | 294/1.2 |
| 5,114,686 | 5/1992 | Gillespie | 206/5.1 X |
| 5,167,323 | 12/1992 | Ohta et al. | 206/5.1 |
| 5,246,259 | 9/1993 | Hellenkamp et al. | 294/1.2 |

*Primary Examiner*—Johnny D. Cherry
*Attorney, Agent, or Firm*—Brumbaugh, Graves, Donohue & Raymond

[57] ABSTRACT

Apparatus is provided for retaining and applying a contact lens, particularly a disposable, extended-wear lens that tends to be difficult to handle and apply. The apparatus includes a base with a concave cavity that receives an applicator wand with an upper lens receptacle. A retaining member holds the lens and wand in place until the user desires to apply it. Application of the lens can be effected without touching the lens.

7 Claims, 4 Drawing Sheets

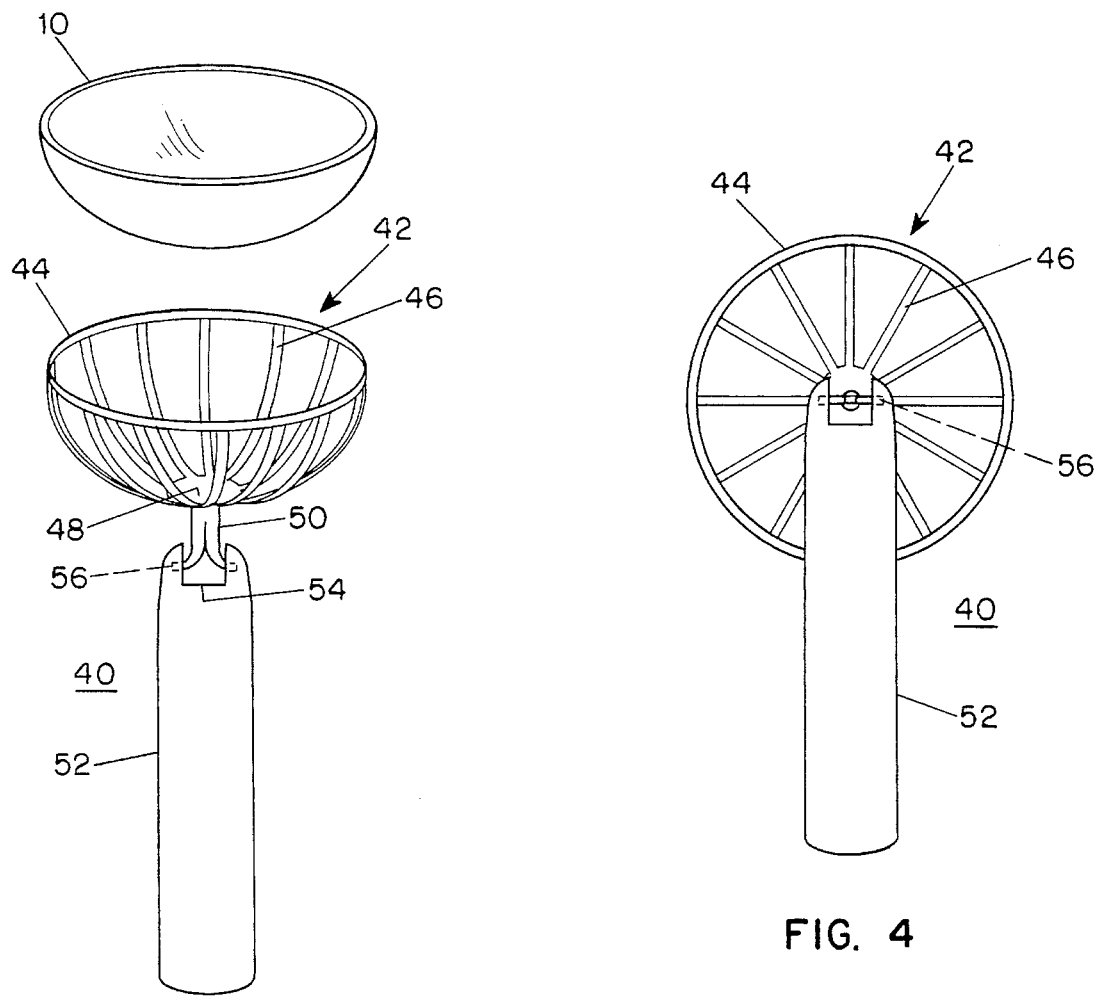
FIG. 3
FIG. 4
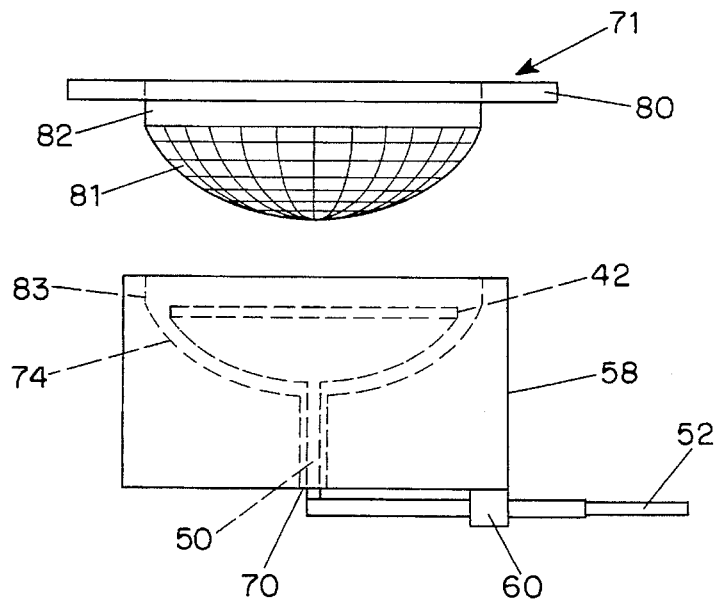
FIG. 5

CONTACT LENS APPLICATOR

RELATED APPLICATION

This application is a continuation-in-part of application Ser. No. 08/279,253, filed Jul. 21, 1994, now U.S. Pat. No. 5,407,244

BACKGROUND OF THE INVENTION

The present invention relates to devices for applying contact lenses, and particularly to applying "disposable" contact lenses which are designed for single use and extended wear. Such disposable lenses are supplied in a plastic pouch filled with fluid. When the package is opened, the user must locate the lens in the fluid and manipulate the lens between the fingers to get the lens in condition for application. Since the lens is very thin and flexible, it will frequently fold upon itself or switch to an "inverted" position that is improper for application.

It is an object of the invention to provide an apparatus that provides a convenient packaging for a disposable lens as well as an apparatus for holding the lens while it is applied, such that the lens can be removed from a fluid filled pouch while in the apparatus, drained of excess fluid and applied, to the user's eye without manual manipulation or hand contact.

SUMMARY OF THE INVENTION

In accordance with the present invention there is provided an apparatus for retaining and applying a contact lens, comprising a base member having a concave upper chamber having a diameter larger than the lens and an applicator wand having a cup-shaped upper receptacle having radially extending fingers connected to a peripheral ring. The peripheral ring is smaller in diameter than the lens and the receptacle is receivable in the concave chamber. The applicator wand includes a handle portion connected to the center of the receptacle and removably extending through an opening in the base member. There is finally provided a fluid permeable retaining member having a convex lower surface for insertion into the concave upper chamber and for releasably attaching thereto to hold a lens in the concave chamber against the upper receptacle.

In a preferred embodiment the cup-shaped upper receptacle is fabricated from surgical rubber to provide flexibility. The handle portion may be flat for easy gripping and be pivotably connected to the cup-shaped receptacle. The opening in the base member may be formed as a slot to receive the flat handle portion and the base member may include a retaining member to releasably retain the handle in a pivoted condition to thereby retain the applicator wand in the concave chamber.

For a better understanding of the present invention, together with other and further objects, reference is made to the following description, taken in conjunction with the accompanying drawings and its scope will be pointed out in the appended claims.

BRIEF DESCRIPTION OF THE DRAWINGS

FIG. 3 is a perspective view of another embodiment of the applicator wand of the present invention.

FIG. 4 is an elevation view of the FIG. 3 applicator wand in the pivoted condition.

FIG. 5 is a side view of the FIG. 3 applicator wand mounted in a base.

DESCRIPTION OF THE PREFERRED EMBODIMENTS

Figure 1:
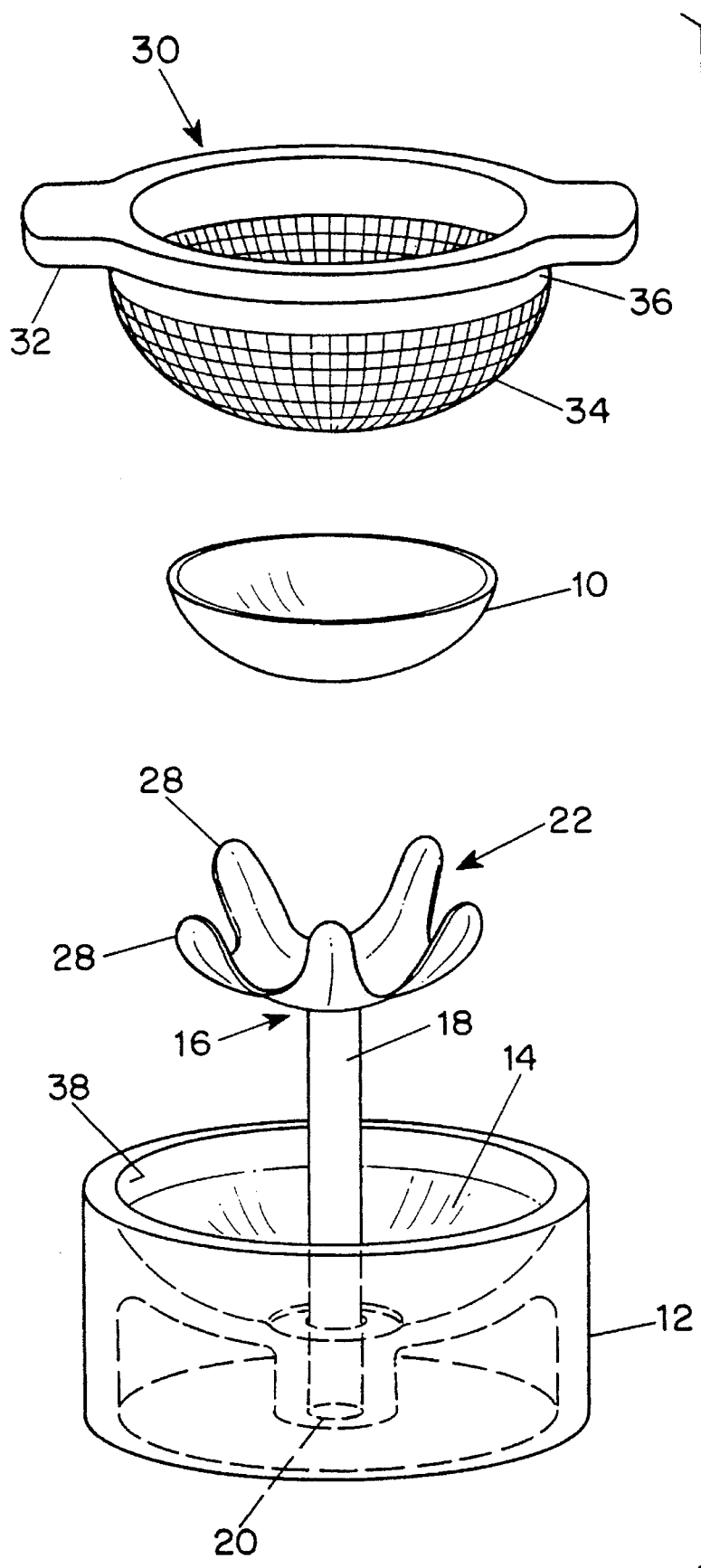
FIG. 1 is a perspective view of the apparatus of the present invention with the parts separated.
Figure 2:
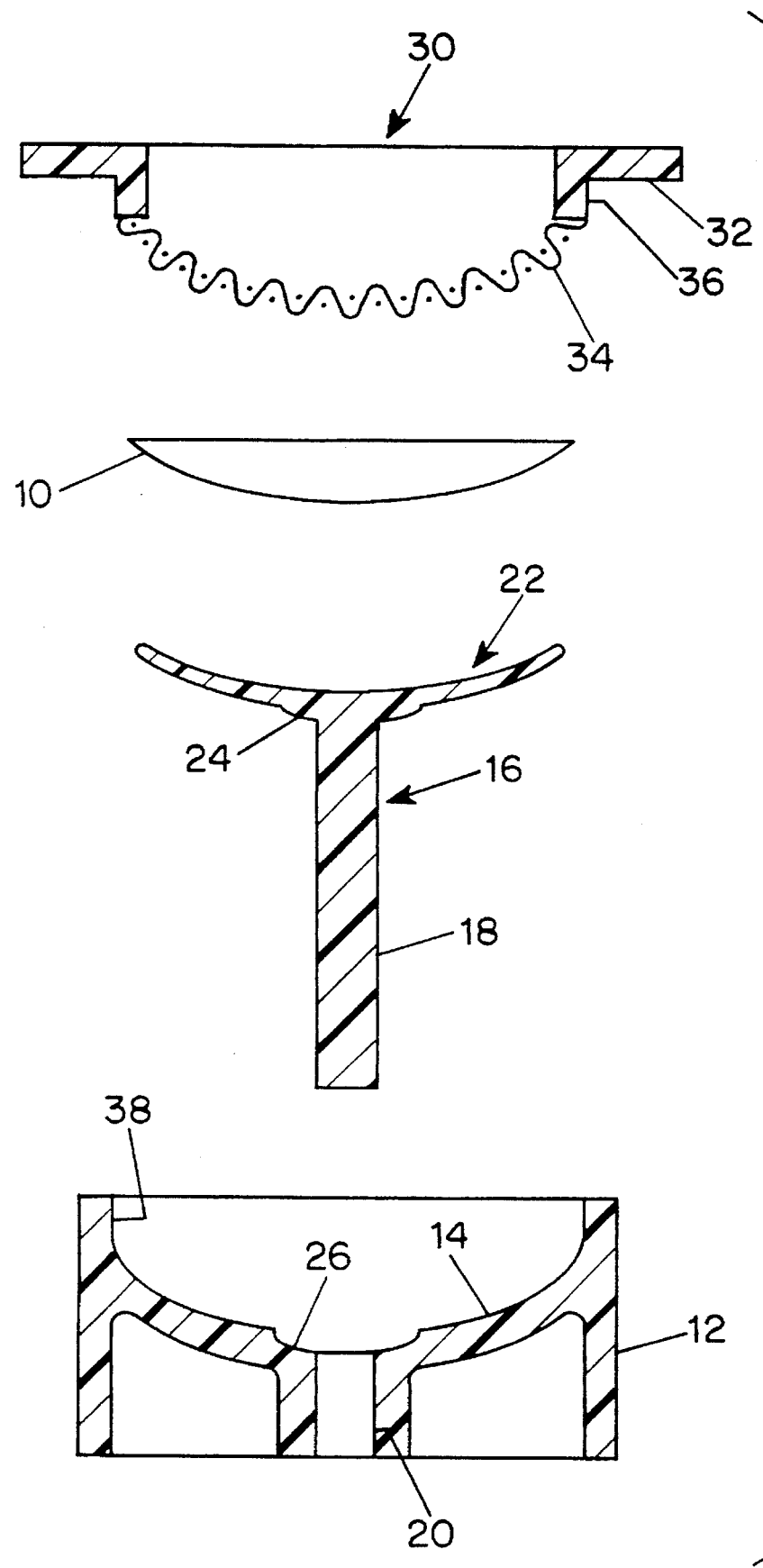
FIG. 2 is a cross sectional view of the FIG. 1 apparatus.

The perspective view of FIG. 1 and cross-section of FIG. 2 show the three parts of an apparatus according to one embodiment of my invention with a contact lens 10 in position to be retained and held by the apparatus. The apparatus includes a base member 12, which is cylindrical in shape and includes an upper concave chamber 14. An applicator wand 16 is receivable in base member 12 by having its shaft 18 pass through a central bore 20 in base 12 and having an upper receptacle 22 of applicator wand 16 received in concave chamber 14.

The diameter of concave chamber 14 is selected to be larger than the diameter of a contact lens 10 to be received therein. The receptacle 22 is smaller in diameter than the lens 10, such that when placed on the receptacle 22, the edges of lens 10 extend beyond the periphery of receptacle 22. Preferably, the base of concave chamber 14 is contoured to receive receptacle 22 and other structure of wand 16, such as receptacle base 24, which is receivable in recess 26. Receptacle 22 in one embodiment comprises flexible fingers 28 arranged as petals of a flower, and there may also be provided recesses in concave chamber 14 corresponding to fingers 28.

Retaining member 30 has an upper flange 32 with integrally formed tabs and a lower convex mesh surface 34 arranged for insertion into concave chamber 14 of base 12. A cylindrical portion 36 is arranged to fit closely into cylindrical portion 38 of concave chamber 14 and be retained therein.

When assembled, shaft 18 of wand 16 is pulled all the way into base 12 until receptacle 22 sits on the base of concave chamber 14. Lens 10 is placed in position on receptacle 22 and retaining member 30 is placed over the lens and pressed into the concave chamber such that cylindrical surfaces 36, 38 hold retaining member 30 in position and the convex mesh surface 34 of retaining member 30 holds lens 10 in position. The entire assembly can then be packaged in fluid.

When the user desires to apply the lens he can first remove the assembly from the fluid package and drain the fluid from the lens through mesh 34. To aid in the drainage of fluid, base 12 and receptacle 22 may also be provided with drainage openings. By shaking the assembly or blowing through retaining member 30, the lens can be sufficiently dehydrated for application. Blowing also causes the lens to seat against receptacle 22. The retaining member is then removed using flange 32 while holding base 12. After the retaining member is removed, shaft 18 can be pushed upward and the lens can be presented to the eye with the wand in the position shown in FIG. 1. The user can conveniently grasp base 12 to hold the apparatus. Alternatively, wand 16 can be pushed upward until its upper portion can be grasped by the fingers and then removed from base 12 for presenting the lens in receptacle 22 for insertion into the eye. Thus, the lens can be inserted completely without touching and is presented without possibility of inadvertent inversion. Since the lens 10 is larger than receptacle 22, the receptacle does not touch the eye. Accordingly, possibility of lens contamination is largely avoided, and the difficulty of finding a tiny lens and manipulating the same is eliminated.

FIG. 3 shows an alternate embodiment 40 of the applicator wand wherein the cup-shaped upper receptacle 42 is fabricated from surgical rubber to provide a soft texture that will not irritate the eye tissue if inadvertent contact occurs. The receptacle includes a peripheral ring 44 to which fingers 46 are connected. The peripheral ring 44 is smaller in diameter than lens 10. Fingers 46, also of surgical rubber, are connected at the center to mounting piece 50 on the lower side of hub 48.

In the FIG. 3 embodiment, handle 52 has a flat configuration to facilitate gripping as will be further illustrated. Handle 52 has a rectangular cut-out 54 at its upper end. The inside edges include a pair of oppositely facing holes along axis 56 into which prongs on mounting piece 50 of receptacle 42 are received. Handle 52 is made of conventional plastic material, such as polypropylene. The mounting arrangement allows receptacle 42 to pivot about axis 56 to the position shown in FIG. 4.

As shown in FIG. 5, the applicator wand can be used in conjunction with a base member 58 and a retaining member 71, as explained above. The base member 58 is cylindrical in shape and includes an upper concave chamber 74. The applicator wand is receivable in base member 58 by having its handle 52 pass through slot 70 in base 58 and having an upper receptacle 42 of the applicator wand received in concave chamber 74. The handle 52 can then be pivoted as shown in FIG. 5 so that it lies parallel to the bottom of base 58. A retaining member 60, such as a pair of notched protrusions, is provided to releasably maintain the handle 52 in a pivoted condition and also keep the receptacle 42 in position in the base until just prior to use. The retaining member 71 has an upper flange 80 with integrally formed tabs and a lower convex mesh surface 81 arranged for insertion into concave chamber 74 of base 58. A cylindrical portion 82 is arranged to fit closely into cylindrical portion 83 of concave chamber 74 and be retained therein. When the lens is to be applied, the handle 52 is released from the retaining member 60 and pivoted to the straight condition so that it can pass outward through the slot in base 58. Prior to removal of the retaining member 71 from base 58, it has been found to be effective in removing excess fluid from the lens to have the user blow onto the lens from the side away from handle 52. This also assures that the lens is firmly in place in the upper receptacle 42.

Figure 6:
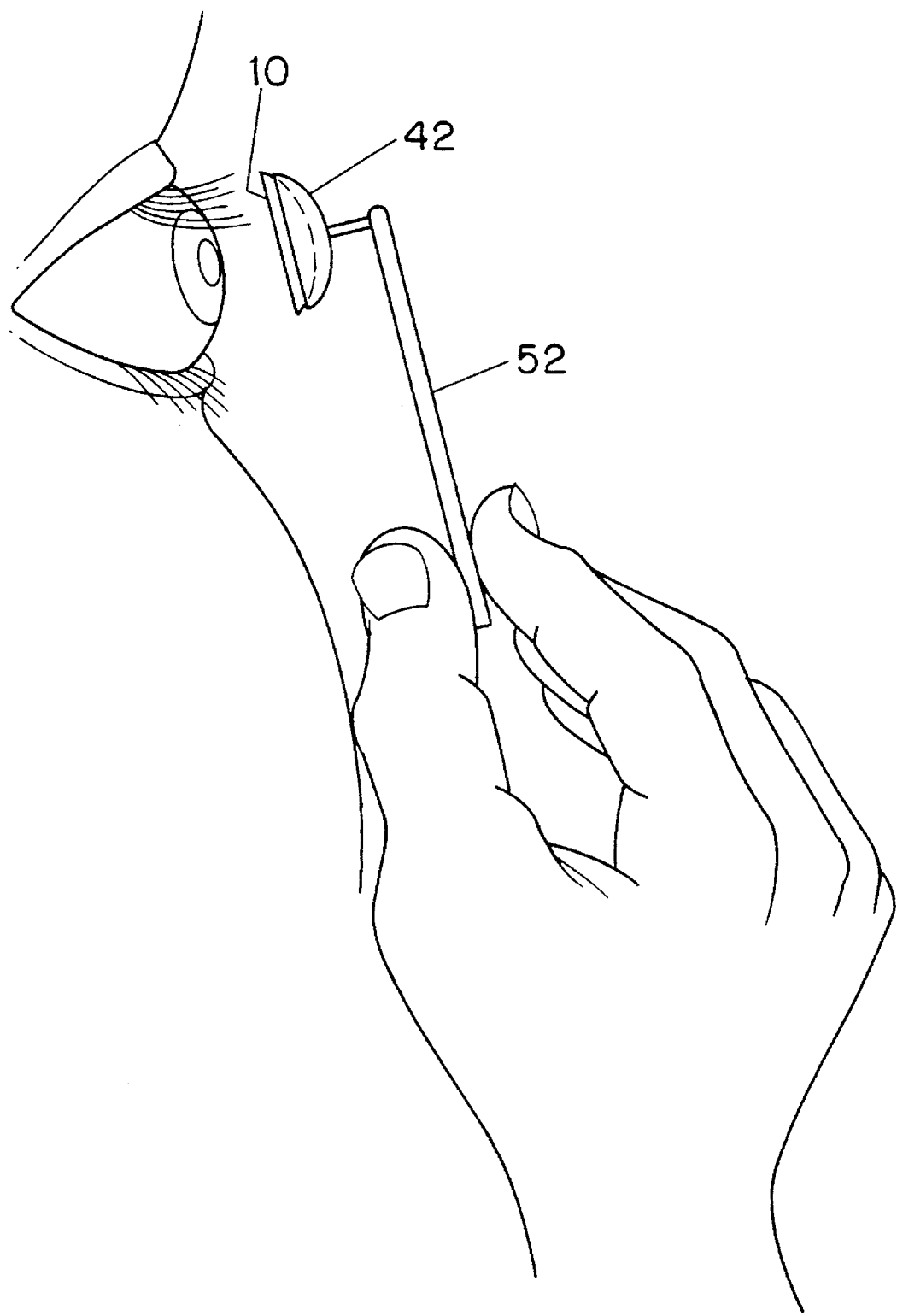
FIG. 6 is a sketch showing the use of the FIG. 3 applicator wand in applying a lens to an eye.

After removing the applicator wand from the base, the handle is preferably pivoted so that the lens may be applied to the eye while the user steadies his thumb against the cheek, as shown in FIG. 6. Accordingly, the pivoting applicator wand of FIG. 3 provides a convenient and natural manipulation for applying a lens.

While there has been described the preferred embodiment of the invention, those skilled in the art will recognize that other and further changes may be made thereto without departing from the spirit of the invention and it is intended to claim all such changes as fall within he true scope of the invention.

I claim:

1. Apparatus for retaining and applying a contact lens, comprising:

a base member having a concave upper chamber, said chamber being larger in diameter than said lens;

an applicator wand having a cup-shaped upper receptacle having radially extending fingers connected to a peripheral ring, said peripheral ring being smaller in diameter than said lens, said receptacle being receivable in said concave chamber and a handle portion connected to the center of said receptacle and removably extending through an opening in said base member; and a fluid permeable retaining member having a convex lower surface for insertion into said concave upper chamber and being arranged to releasably connect to said base member to hold a lens in said concave chamber against said upper receptacle.

2. Apparatus as specified in claim 1 wherein said cup-shaped upper receptacle is fabricated from surgical rubber.

3. Apparatus as specified in claim 1 wherein said handle portion is pivotably connected to said cup-shaped upper receptacle.

4. Apparatus as specified in claim 3, wherein said handle portion is flat and said opening in said base member comprises a slot.

5. Apparatus as specified in claim 4, wherein said base member includes retaining means on a side opposite said upper chamber for releasably maintaining said handle portion in a pivoted condition, thereby retaining said applicator wand in said concave chamber.

6. An applicator wand for applying a contact lens to an eye comprising a cup-shaped receptacle for receiving said lens and formed of surgical rubber, said receptacle having radially extending fingers connected to a peripheral ring, said peripheral ring being smaller in diameter than said lens;

a mounting piece connected to a central portion of said receptacle, said mounting piece having a plurality of prongs; and a handle having an upper end cut-out to receive said prongs so that the handle is pivotably mounted to the central portion of said receptacle.

7. An applicator wand as specified in claim 6 wherein said handle is flat.

\* \* \* \* \*